United States Patent [19]

Rooke et al.

[11] Patent Number: 4,537,887

[45] Date of Patent: Aug. 27, 1985

[54] PHARMACEUTICAL FORMULATION

[75] Inventors: David J. Rooke, Horsham; Barry W. Burnstead, Littlehampton, both of England

[73] Assignee: Beecham Group Limited, England

[21] Appl. No.: 539,099

[22] Filed: Oct. 5, 1983

Related U.S. Application Data

[63] Continuation of Ser. No. 478,151, Mar. 23, 1983, , which is a continuation of Ser. No. 303,786, Sep. 21, 1981, abandoned.

[30] Foreign Application Priority Data

Sep. 27, 1980 [GB] United Kingdom ................ 8031298

[51] Int. Cl.³ .................... A61K 31/43; A61K 31/42; A61K 47/00
[52] U.S. Cl. .................................. 514/197; 514/210; 514/770
[58] Field of Search ................ 424/271, 272, 357, 23, 424/114

[56] References Cited

U.S. PATENT DOCUMENTS

| | | | |
|---|---|---|---|
| 4,140,755 | 2/1979 | Sheth et al. | 424/22 |
| 4,226,849 | 10/1980 | Schor | 424/22 |
| 4,282,202 | 8/1981 | Dowrick | 424/357 |

FOREIGN PATENT DOCUMENTS 0132788 11/1969 Czechoslovakia .

*Primary Examiner*—Frederick E. Waddell
*Assistant Examiner*—John W. Rollins
*Attorney, Agent, or Firm*—Jacobs & Jacobs

[57] ABSTRACT

A unit dose pharmaceutical composition suitable for oral administration which composition comprises a pharmaceutically acceptable carrier, a desiccant, amoxycillin trihydrate equivalent to 20 mg to 1500 mg of amoxycillin and potassium clavulanate equivalent to 20 mg to 500 mg of clavulanic acid, with the proviso that the weight ratio of amoxycillin to clavulanic acid is in the range 12:1 to 1:1; characterized in that the composition is in tablet form, wherein the desiccant is edible and incorporated within the tablets.

12 Claims, No Drawings

PHARMACEUTICAL FORMULATION

CROSS REFERENCE

This is a continuation of Ser. No. 478,151, filed Mar. 23, 1983, which is a continuation of Ser. No. 303,786 filed Sept. 21, 1981, now abandoned.

The present invention relates to pharmaceutical compositions for oral administration in the treatment of bacterial infections.

West German OLS No 2843318 discloses pharmaceutical compositions suitable for oral administration which comprise 20 mg to 1500 of amoxycillin trihydrate, 20 mg to 500 mg of potassium clavulanate and a pharmaceutically acceptable carrier with the proviso that the weight ratio of amoxycillin trihydrate to potassium clavulanate is from 6:1 to 1:1.

DE-OS No 2843318 further discloses a packaged pharmaceutical composition of enhanced storage stability which comprises a container closed to prevent ingress of moisture and which contains one or more unit-dose compositions as described above together with a desiccant. Suitable non-toxic desiccants are disclosed as being included in sachets or capsules within the packaging or enclosed in a receptacle or separate compartment, for example in the cap or on the floor of the container.

It has not been found that tablet formulations incorporating an edible desiccant within the tablet itself can be prepared. In addition to facilitating processing and handling of the formulation mix prior to compressing into tablets, the tablets are less susceptible to faults or imperfections in the packaging for the tablets, which may allow ingress of water vapour and hence degradation. Incorporation of the desiccant into the tablet obviates the need for special pack inserts containing desiccant as described in DE-OS 2843318.

Accordingly, the present invention provides a unit-dose pharmaceutical composition suitable for oral administration which composition comprises a pharmaceutically acceptable carrier, a desiccant, amoxycillin trihydrate equivalent to 20 mg to 1500 mg of amoxycillin and potassium clavulanate equivalent to 20 mg to 500 mg of clavulanic acid, with the proviso that the weight ratio of amoxycillin to clavulanic acid is in the range 12:1 to 1:1; characterised in that the composition is in tablet form, wherein the desiccant is edible and incorporated within the tablets.

The weights of amoxycillin trihydrate and potassium clavulanate are referred to herein in terms of the weights of the pure free acids (pfa) amoxycillin and clavulanic acid respectively.

Suitably the weight ratio of amoxycillin to clavulanic acid in the pharmaceutical composition of the present invention is from 8:1 to 2:1 for example 5:1, 4:1, 3:1 or 2:1. Preferred weight ratios of amoxycillin to clavulanic acid are 8:1, 4:1 and 2:1.

In general the oral dosage unit of this invention will contain from 125 mg to 1250 mg of amoxycillin, for example it may contain about 125, 250, 500 or 1000 mg of amoxycillin.

In general the dosage unit of this invention will contain from 20 to 300 mg of clavulanic acid for example it may contain about 25, 31.25, 50, 62.5, 100, 120, 125, 150, 200, 250 or 300 mg of clavulanic acid.

From the foregoing it will be realised that certain perferred compositions of this invention comprise from 80 mg to 600 mg of amoxycillin and from 20 mg to 300 mg of clavulanic acid with the proviso that the weight ratio of amoxycillin to clavulanic acid is either 2:1, 4:1 or 8:1.

Suitable amounts of clavulanic acid for use in those compositions include the aforementioned approximately 25, 31.25, 50, 62.5, 100, 120, 125, 150, 200, 250 or 300 mgs.

Certain preferred compositions of this invention will contain about 125–500 mg of amoxycillin and about 31.25–125 mg of clavulanic acid.

Suitable desiccants which may be used in the present invention include edible grades of silica gel or crystalline sodium, potassium or calcium aluminosilicate (commonly termed "Molecular Sieves").

A preferred edible grade of silica gel is Syloid AL/1 (Syloid AL/1 is manufactured by W R Grace Ltd, Northdale House, North Circular Road, London.), which is a colloidal silica having an average particle size of 8 $\mu$m and a BET specific surface area of about 750 $m^2/g$.

A preferred edible grade of Molecular Sieve is sodium aluminosilicate sold under the trade name Molcular Sieve Type 4A by Union Carbide Corporation.

The desiccant will generally represent between 2% and 25% of the total weight of the formulated tablet. Most suitably the desiccant will be present in an amount weight for weight less than that of the antibacterially active ingredients. Preferably the desiccant will represent 2.5 to 10% of the total weight of the formulated tablet, a particularly favoured amount is 5% w/w of the tablet.

In addition to the antibacterially active ingredients and the desiccant present in the tablets, such compositions may contain one or more conventional fillers such as microcrystalline cellulose, lubricants such as magnesium stearate, disintegrants such as sodium starch glycollate, crosslinked polyvinyl pyrrolidone or other similar known agents. In addition such compositions may contain flavouring agents, preservatives and colouring agents. The materials present in such compositions should have low free moisture contents and preferably be pre-dried. Tightly bound water, such as water of crystallisation normally has little adverse effect on stability.

Other typical agents which may be used in the carrier include microfine cellulose (as a filler), calcium carbonate or magnesium carbonate (usually light magnesium carbonate) (as fillers) and starch or crosslinked polyvinyl pyrrolidone (as a disintegrant).

The tablets according to this invention may be film coated, if desired, with normal agents such as hydroxypropylmethyl cellulose, or with a coat that delays ingress of moisture. Suitable agents for such film coats include methacrylate polymers, methacrylic acid methacrylate copolymers, and natural resins such as shellec or copal resins or their conventional modifications.

Alternatively the coating may be an enteric coating, ie a coating that is insoluble in acidic gastric juice but soluble in alkaline digestive juice; such a coating enables the medicament to pass through the stomach into the duodenum, from where it is absorbed. Suitable enteric coatings include cellulose acetate phthalate.

The compositions of the present invention are suitably packaged in protective packages such as, for example, screw-cap bottles, aluminium foil sachets and aluminium bister packs.

Also included within the scope of the present invention is a process for the preparation of a tablet composition as hereinbefore described which comprises bringing into association the components of said composition and thereafter compressing the blended mixture into a tablet.

It is preferable that the formulation of the composition is carried out in a dry atmosphere, eg one containing less than 30% relative humidity and preferably one containing less than 20% relative humidity.

In the following examples, which illustrate the invention, the compositions were formulated under a dry atmosphere.

Tablets of the following compositions were prepared:

EXAMPLE 1

| Ingredients | % w/w |
| --- | --- |
| Amoxycillin trihydrate as free acid | 16.25 |
| Potassium clavulanate as free acid | 4.063 |
| Syloid AL/1 | 5.00 |
| Flavours | 10.50 |
| Crosslinked polyvinyl pyrrolidone | 6.875 |
| Magnesium stearate | 0.625 |
| Microcrystalline cellulose (Avicel PH102) | to 100.00 |

EXAMPLE 2

| Ingredients | % w/w |
| --- | --- |
| Amoxycillin trihydrate as free acid | 15.294 |
| Potassium clavulanate as free acid | 7.65 |
| Sodium Alumino silicate | 5.00 |
| Flavours | 10.00 |
| Crosslinked polyvinyl pyrrolidone | 6.47 |
| Magnesium stearate | 0.59 |
| Microcrystalline cellulose (Avicel PH102) | to 100.00 |

EXAMPLE 3

| Ingredients | % w/w |
| --- | --- |
| Amoxycillin trihydrate as free acid | 15.294 |
| Potassium clavulanate as free acid | 3.823 |
| Sodium Alumino silicate | 5.00 |
| Flavours | 10.00 |
| Crosslinked polyvinyl pyrrolidone | 6.47 |
| Magnesium stearate | 0.59 |
| Microcrystalline cellulose (Avicel PH102) | to 100.00 |

EXAMPLE 4

| Ingredients | % w/w |
| --- | --- |
| Amoxycillin trihydrate as free acid | 16.25 |
| Potassium clavulanate as free acid | 8.125 |
| Syloid AL/1 | 5.00 |
| Flavours | 10.00 |
| Crosslinked polyvinyl pyrrolidone | 6.875 |
| Magnesium stearate | 0.625 |
| Microcrystalline cellulose (Avicel PH102) | to 100.00 |

EXAMPLE 5

| Ingredients | 375 mg | % w/w | 625 mg | % w/w |
| --- | --- | --- | --- | --- |
| Potassium Clavulanate = pfa | 125.00 | 16.34 | 125.00 | 11.90 |
| Amoxycillin Trihydrate = pfa | 250.00 | 32.68 | 500.00 | 47.62 |
| Colloidal Silica | 7.65 | 1.00 | 10.50 | 1.00 |
| Sodium Starch Glycollate | 11.00 | 1.44 | 21.00 | 2.00 |
| Silica Gel (Syloid AL/1) | 76.50 | 10.00 | 31.50 | 3.00 |
| Magnesium Stearate | 4.85 | 0.63 | 7.27 | 0.69 |
| Microcrystalline Cellulose | 765.00 | to 100.0 | 1050.00 | to 100.0 |
| Film Coat | | | | |
| Titanium dioxide suspension solid residue | 4.00 | | 5.56 | |
| Ethylcellulose | 2.26 | | 3.15 | |
| Diethyl Phthalate | 2.67 | | 3.70 | |
| Hydroxypropylmethyl cellulose | 9.07 | | 12.59 | |
| Silicone Cream, non-volatile residue | — | | 0.05 | |
| Film Coated Tablet Weight | 783.0 | | 1075.0 | |

EXAMPLE 6

| Ingredients | 375 mg | % w/w | 281.25 mg | % w/w |
| --- | --- | --- | --- | --- |
| Potassium Clavulanate = pfa | 125.00 | 16.34 | 31.25 | 4.08 |
| Amoxycillin Trihydrate = pfa | 250.00 | 32.68 | 250.00 | 32.68 |
| Colloidal Silica | 7.65 | 1.00 | 7.65 | 1.00 |
| Sodium Starch Glycollate | 11.00 | 1.44 | 11.00 | 1.44 |
| Molecular Sieve 4A | 38.25 | 5.00 | 38.25 | 5.00 |
| Magnesium Stearate | 4.85 | 0.63 | 4.85 | 0.63 |
| Microcrystalline Cellulose to | 765.00 | to 100.00 | 765.00 | to 100.00 |
| Film coat | 18 mg | | 18 mg | |
| Titanium dioxide suspension solid residue | 4.00 | | 4.00 | |
| Ethylcellulose | 2.26 | | 2.26 | |
| Diethyl Phthalate | 2.67 | | 2.67 | |
| Hydroxypropyl-methylcellulose | 9.07 | | 9.07 | |
| Silicone Cream, non-volatile residue | — | | — | |
| Film coated tablet weight | 783.0 | | 783.0 | |

I claim:

1. A pharmaceutical composition in unit does tablet form suitable for oral administration to humans and animals which comprises amoxycillin trihydrate equivalent to 20 mg to 1500 mg of amoxycillin, potassium clavulanate equivalent to 20 mg to 500 mg of clavulanic acid, the weight ratio of amoxycillin to clavulanic acid being in the range of from 12:1 to 1:1, an effective amount of a colloidal silica having an average particle size of 8 μm and a BET specific surface area of about 750 m$^2$/g incorporated within each tablet as a desiccant, and a pharmaceutically acceptable carrier suitable for tablets.

2. A composition according to claim 1 wherein the ratio of amoxycillin to clavulanic acid is from 8:1 to 2:1.

3. A composition according to claim 1 wherein the ratio of amoxycillin to clavulanic acid is 8:1, 4:1 or 2:1.

4. A composition according to claim 1 which contains amoxycillin trihydrate equivalent to 125–500 mg of amoxycillin.

5. A composition according to claim 1 which contains potassium clavulanate equivalent to 31.25 to 125 mg of clavulanic acid.

6. A composition according to claim 1 wherein the colloidal silica is present in an amount of from 2% to 25% of the total weight of the formulated tablet.

7. A composition according to claim 1 wherein the colloidal silica is present in an amount of from 2.5% to 10% of the total weight of the formulated tablet.

8. A composition according to claim 1 wherein the colloidal is present in an amount of from about 5% w/w of the formulated tablet.

9. A composition according to claim 1 packaged in a protective package.

10. A process for the preparation of a composition of claim 1 which comprises formulating unit dose tablets by mixing together an amount of amoxycillin trihydrate equivalent to 20 mg to 1500 mg of amoxycillin, an amount of potassium clavulanate equivalent to 20mg to 500 mg of clavulanic acid, the weight ratio of amoxycillin to clavulanic acid being in the range of from 12:1 to 1:1, an effective amount of a colloidal silica having an average particle size of 8 $\mu$m and a BET specific surface area of about 750 $m^2/g$ as a desiccant and an effective amount of a pharmaceutically acceptable carrier suitable for tablets.

11. A process according to claim 10 wherein the formulation is carried out in an atmosphere containing less than 30% relative humidity.

12. A process according to claim 10 wherein the formulation is carried out in an atmosphere containing less than 20% relative humidity.

* * * * *